United States Patent
Caron (10) Patent No.: US 7,441,660 B2
(45) Date of Patent: Oct. 28, 2008

(54) PACKAGING AND DISPLAY BOX FOR AN OSTEOSYNTHESIS ASSEMBLY, PROTECTIVE SET AND DISPLAY CASE COMPRISING SAME

(76) Inventor: Philippe Caron, 22 Rue Nansouty B.P. 1040, Papeete (PF) Pf-98713

( * ) Notice: Subject to any disclaimer, the term of this patent is extended or adjusted under 35 U.S.C. 154(b) by 515 days.

(21) Appl. No.: 10/510,464

(22) PCT Filed: Mar. 20, 2003

(86) PCT No.: PCT/FR03/00885

§ 371 (c)(1),
(2), (4) Date: Mar. 24, 2005

(87) PCT Pub. No.: WO03/079918

PCT Pub. Date: Oct. 2, 2003

(65) Prior Publication Data

US 2005/0173278 A1 Aug. 11, 2005

(30) Foreign Application Priority Data

Mar. 22, 2002 (FR) .................................. 02 03594

(51) Int. Cl.
*B65D 83/10* (2006.01)
(52) U.S. Cl. ...................... 206/570; 206/370; 206/438
(58) Field of Classification Search ................ 206/581, 206/570, 363, 370, 438, 439, 828, 775
See application file for complete search history.

(56) References Cited

U.S. PATENT DOCUMENTS

| 4,936,463 A | * | 6/1990 | Tiramani ..................... 206/581 |
| 5,005,697 A | * | 4/1991 | Jimbo et al. ................. 206/235 |
| 5,732,821 A | | 3/1998 | Stone et al. |
| 5,941,255 A | * | 8/1999 | Chen .......................... 132/315 |

FOREIGN PATENT DOCUMENTS

| DE | 297 05 944 | 5/1997 |
| EP | 0 290 138 | 11/1988 |
| WO | WO 00/57810 | 10/2000 |
| WO | WO 01/52762 | 7/2001 |

\* cited by examiner

*Primary Examiner*—Jacob K Ackun, Jr.
(74) *Attorney, Agent, or Firm*—Merchant & Gould P.C.

(57) ABSTRACT

The present invention relates to a packaging and display box (100) for an osteosynthesis kit (10) comprising at least one plate (12) and at least one osteosynthesis screw (14). According to the invention, the box comprises at least a lid portion (120) and a bottom portion (110) defining a storage space (130), said lid portion (120) being made to be movable relative to said bottom portion by functional means (160). The box further comprises closure means (170). The box further comprises housing means (140) for housing said osteosynthesis kit (10) and suitable for being retained in said storage space (130), the housing means comprising at least one insert (142, 144) and being provided with at least one cavity (142) for receiving at least one plate (12) and at least one cell (144a) for receiving at least one screw (14).

18 Claims, 6 Drawing Sheets

PACKAGING AND DISPLAY BOX FOR AN OSTEOSYNTHESIS ASSEMBLY, PROTECTIVE SET AND DISPLAY CASE COMPRISING SAME

FIELD OF INVENTION

The present invention relates to a packaging and display box for an osteosynthesis kit, said kit comprising at least one plate and at least one screw.

BACKGROUND OF THE INVENTION

Osteosynthesis screws and plates are used for reducing bone fractures, specifically for putting two bone fragments back into position relative to each other and for holding them in position.

Such osteosynthesis screws and plates are conventionally used in particular during maxillo-facial surgery, whether for repair purposes in order to reduce an accidental fracture, or for functional and/or plastic surgery purposes as is the case with osteotomies of the upper or lower jaw.

During such surgery, the surgeon has available a set of plates and a set of fixing screws that have previously been extracted from their respective packaging (e.g. from a receptacle containing plates and from another receptacle containing fixing screws) prior to being sterilized and then put on a tray that remains available throughout the surgery.

Depending on the type of intervention that is to be performed, the set of plates may comprise one or more optionally identical plates, and the set of screws may comprise one or more optionally identical screws. These sets are generally constituted by more than a single piece since even when only one piece is required for the surgery, it is necessary to have at least one other piece available as a spare in the event of the first piece to be handled being mechanically defective or no longer in a satisfactory aseptic state.

In addition, even when the type of plate and the type of screw that is to be used have been established beforehand, uncertainty can subsist as to the dimensions that are best suited to the morphology of the patient, in particular concerning the length of the screws to be used.

Consequently, numerous handling operations are required on those elements (plates and screws) forming the osteosynthesis kit, before, during, and after surgery:

before surgery: operating theater personnel must prepare the elements of the osteosynthesis kit, i.e. determine the type(s) of screw and plate to be provided, and also the number(s) thereof, find them in stock, and then sterilize them and put them into sealed envelopes; the elements are then allowed to wait until shortly before surgery, at which moment the sealed envelopes are opened and the elements are placed on the above-mentioned tray;

during surgery: some or all of the elements of the osteosynthesis kit will be taken in forceps or some other suitable instrument prior to being put into place and fixed to the patient using instruments designed for this purpose; the forceps (or other instrument) going back and forth between the tray and the patient or the above-mentioned instruments, leads to a risk of dirtying and contaminating elements that have not yet been used and that remain on the tray; and after surgery: from the above, those elements that remain and that have not been damaged from a mechanical point of view need to be subjected to a new step of cleaning and sterilization, regardless of whether or not they have been touched by an instrument, prior to being returned to stock waiting to be selected for a forthcoming surgical intervention; in other words, under no circumstances are elements that remain still sterile.

An object of the present invention is to solve the above-specified problems so as to enable the amount of handling that needs to be performed in the operating theater to be reduced, including handling concerning sterilization, so as to provide the surgeon with an osteosynthesis kit that is directly suitable for use in the operating theater, while guaranteeing the quality and the sterility of the equipment constituting the osteosynthesis kit.

SUMMARY OF THE INVENTION

To this end, the invention provides a packaging and display box which is characterized in that it comprises a bottom portion and at least one lid portion, said bottom portion comprising a bottom wall and a side wall upwardly extending the bottom wall around its entire periphery, thereby defining a storage space, functional means making said lid portion movable relative to said bottom portion between an open position and a closed position, in that said box further comprises reversible closure means placed on said bottom portion and on said lid portion and suitable for co-operating in said closed position, and in that said box further comprises housing means for housing said osteosynthesis kit, said housing means being suitable for being held in said storage space and comprising at least one insert, said housing means being provided with at least one cavity for receiving at least one osteosynthesis plate and at least one cell for receiving at least one osteosynthesis screw.

It will be understood that the box of the invention thus enables an already prepared and matched osteosynthesis kit to be provided that is directly suitable for use in operating theater.

Such a box is conventionally made of plastics material to keep down expense and weight and must also satisfy the asepsis criteria of an operating theater. When used during surgery, the box is taken directly into the aseptic operating theater.

To this end, in the present invention, provision is made for said box of the invention preferably further to comprise a heat-sealable film enclosing said storage space. In this way, with a sterilization operation being performed under radiation, preferably using gamma rays, the film of heat-sealable plastics material is not damaged and it is guaranteed that the storage space that continues to be closed in sealed manner by the heat-sealable film conserves its sterilized state.

In a preferred solution that makes it possible to provide traceability for the box and the elements it contains constituting the osteosynthesis kit, provision is made for the face of the bottom wall that faces away from said storage space to be provided with an identification medium carrying information relating to said osteosynthesis kit, in particular in the form of a bar code. By way of example, the identification medium is constituted by a label made up of one or more portions.

The present invention also provides a protective unit including the above-specified box, the box being received in a tray defining a housing suitable for receiving said packaging box, which tray is provided with a heat-sealable film enclosing said housing.

In another aspect of the present invention, said protective unit as defined in the preceding paragraph further comprises a protective and packaging case suitable for surrounding said tray.

This serves to increase the number of layers providing the box and its content, i.e. said osteosynthesis kit, with mechanical and/or aseptic protection.

In a preferred embodiment, said protective case carries means for visually identifying the type of osteosynthesis kit that is contained in said packaging box. This makes it possible, merely by looking at the protective case, to determine the makeup and the surgical indication for the osteosynthesis kit contained in the box.

Preferably, said protective case comprises a bottom portion and a lid portion that are movable relative to each other between an open position and a closed position, and said protective case further comprises reversible closure means placed on said bottom portion and on said lid portion and suitable for co-operating in said closed position.

The present invention also provides a display chest for distributing osteosynthesis kits, the chest comprising a bottom portion fitted with compartments each serving to receive a protective unit as defined above, and at least one lid portion that is movable relative to said bottom portion for the purpose of reversibly closing the space defined by the bottom portion, at least in part.

The invention will be better understood and the secondary characteristics and their advantages will appear on reading the description of an embodiment given below by way of example.

It should be understood that the description and the drawings are given purely by way of non-limiting indication.

BRIEF DESCRIPTION OF THE DRAWINGS

Reference is made to the accompanying drawings, in which.

DESCRIPTION OF PREFERRED EMBODIMENTS

Figure 1:
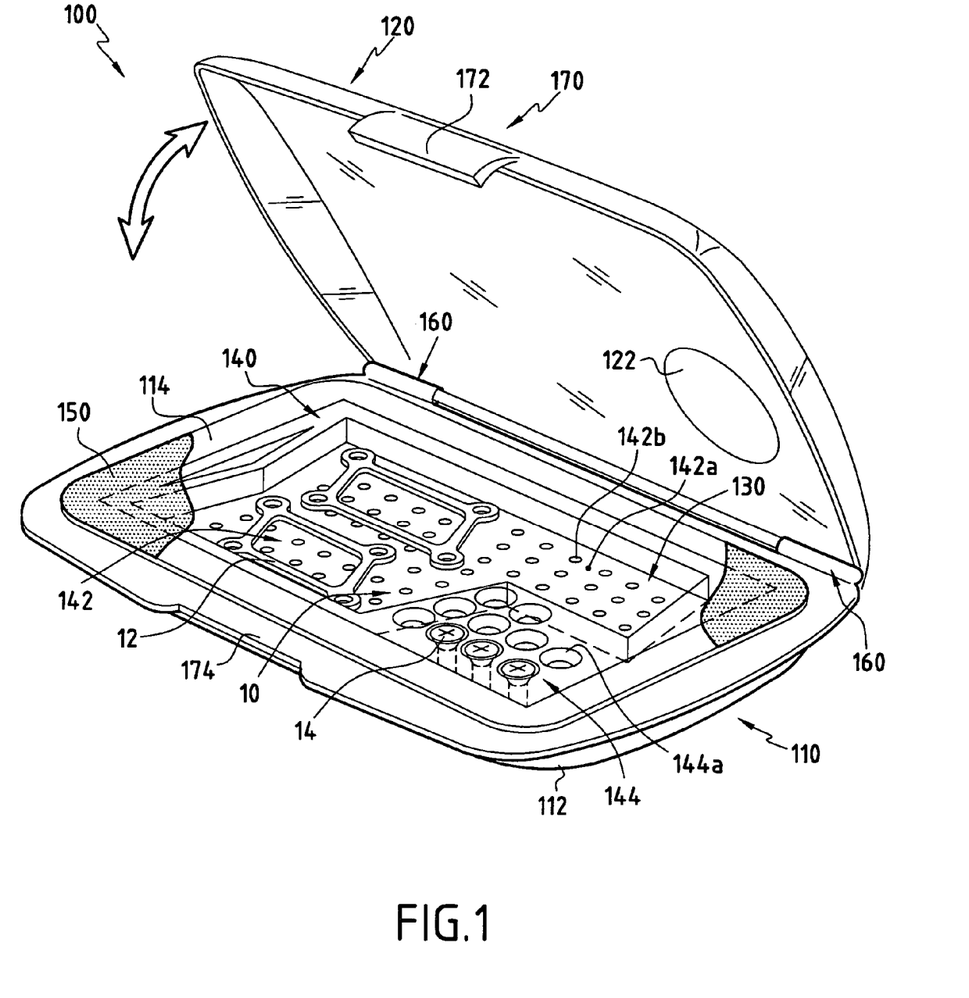
FIG. 1 is a perspective view seen from a front corner and from above showing a packaging and display box for an osteosynthesis kit in accordance with the present invention, in an intermediate position between its closed position and its open position.

The packaging and display box 100 shown in FIG. 1 comprises a bottom portion 110 and a lid portion 120.

The bottom portion 110 and the lid portion 120 are both generally rectangular in shape having the same width and the same length, so that the lid portion 120 is suitable for closing the space 130 defined in the bottom portion 110.

It should be understood that other shapes could also be envisaged for the bottom portion 110 and the lid portion 120 without thereby going beyond the ambit of the present invention, and circular, oval, oblong, square, triangular, parallelogram, polygonal, etc. shapes could equally well be used in the same way.

The bottom portion 110 is constituted by a bottom wall 112 which is extended upwards around its entire periphery by a continuous side wall 114 that forms a closed loop around the space 130. Thus, the bottom wall 112 and the side wall 114 define the storage space 130 that is to receive an osteosynthesis kit 10.

In FIG. 1, the osteosynthesis kit 10 comprises two osteosynthesis plates 12 each in the form of a lozenge-shaped flat plate, and three screws 14.

In order to display the osteosynthesis kit 10 in a manner that serves simultaneously to identify clearly each of the elements of the osteosynthesis kit 10 and to make them easy to grasp individually, the storage space 130 contains housing means in the form of an insert 140 suitable for being made of a rigid molded plastics material, as are the bottom portion 110 and the lid portion 120.

The insert 140 has an outside shape that is complementary to the shape of the storage space 130 defined by the bottom portion 110, so that in normal use the insert 140 remains housed in the storage space 130.

More precisely, and as can be seen in FIG. 1, the insert 140 comprises two distinct zones: a first zone defining a cavity 142 in which there are placed the two plates 12 that are visible in FIG. 1; and a second zone 144 comprising a plurality of cells 144a for housing the screws 14 individually.

In FIG. 1, the cavity 142 has a bottom that is formed by a support face for the osteosynthesis plates, said support face 142a being provided with hollow zones 142b in the form of small depressions.

These hollow zones 142b are suitable for use as one of the elements of retaining means designed to co-operate in reversible manner with an osteosynthesis plate 12 in order to hold it against the support face 142a.

Figure 2:
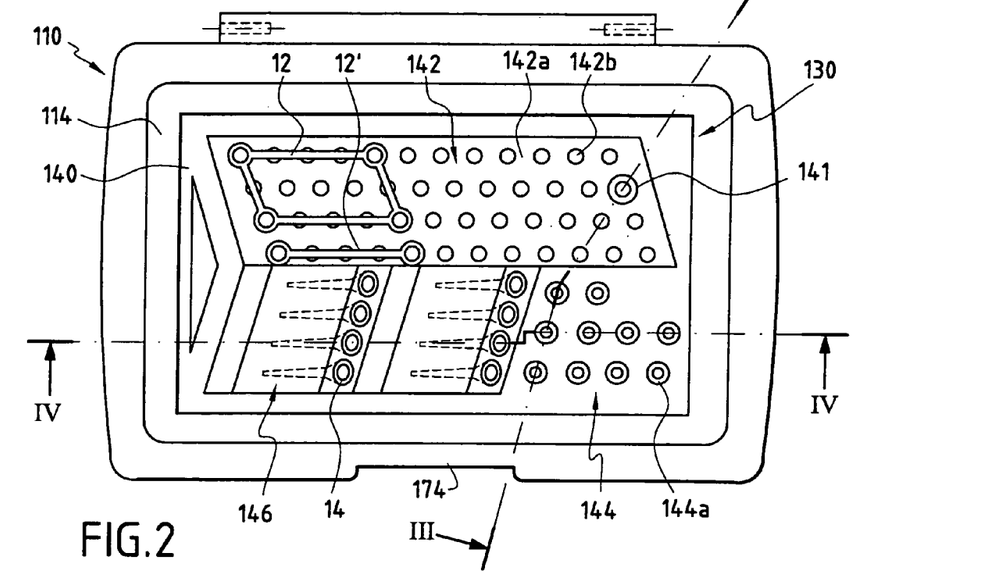
FIG. 2 is a projection view from above of the bottom portion of the FIG. 1 box.
Figure 3:
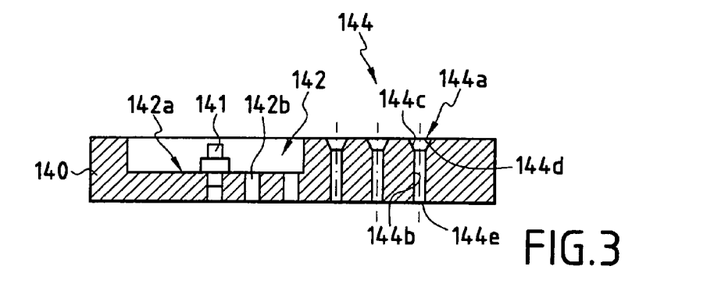
FIG. 3 is a section view on III-III of FIG. 2.

These retaining means are shown more particularly in FIGS. 2 and 3: pegs 141, each comprising two rod portions, are suitable for being received in one of the depressions 142b, with the rod portion then projecting from the hollow zones 142b so as to be suitable for being received in one of the holes in a plate (lozenge-shaped plate 12 or linear plate 12' as shown in FIG. 2). These pegs 141 form the other elements of the above-mentioned retaining means since each peg serves in combination with one of the depressions 142b to hold a plate against the support face 142a at a well-determined location.

In an alternative embodiment, the support face 142a of the cavity 142 of the insert 140 could be provided both with hollow zones and with projecting zones.

Whatever their shape, these portions in relief enable the plates to be raised slightly so as to make them easier to grasp using an instrument such as a forceps, in particular a forceps specially adapted for taking hold of plates of this type.

Figure 5:
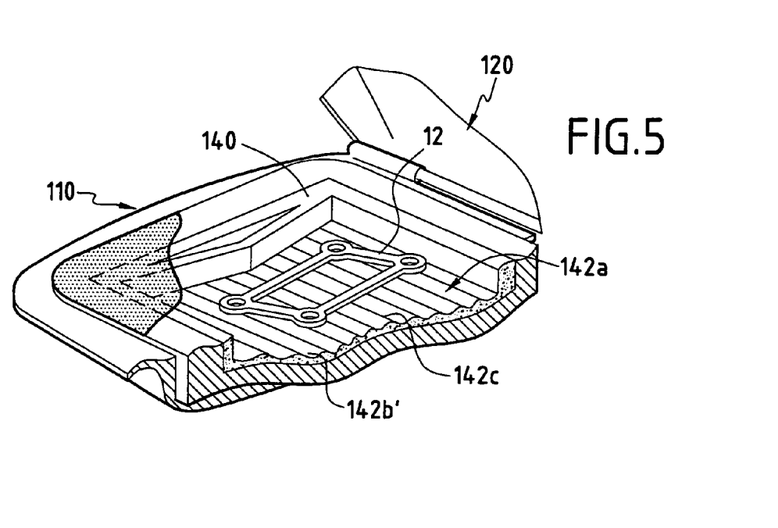
FIG. 5 is a diagrammatic fragmentary perspective view showing an alternative embodiment of the bottom portion of the packaging box of the present invention.

In particular, in a preferred alternative embodiment, the support face 142a of the cavity 142 is provided with ribs 142c and with grooves 142b' that are mutually parallel, so as to form a fluted surface on which the osteosynthesis plate 12 rests, as can be seen in FIG. 5.

Other shapes in relief presenting hollows and projecting zones could naturally be used in the same way.

With reference again to FIG. 1, the second zone 144 of the insert 140, which is shown as forming one of the corners of the storage space 130, has ten cells 144a, each in the form of a hollow recess of a shape that is complementary to the screw that is to be received in said cell.

The cells 144a are made in the form of recesses having a shape enabling the head of the screw 14 to be situated in the opening of the recess 144a. More precisely, the head of the screw 14 is level with, slightly above, or slightly below the plane of the opening 144d of the recess 144a in such a manner as to make it possible in any event to gain access to the head of the screw 14 from said opening 144d.

Figure 4:
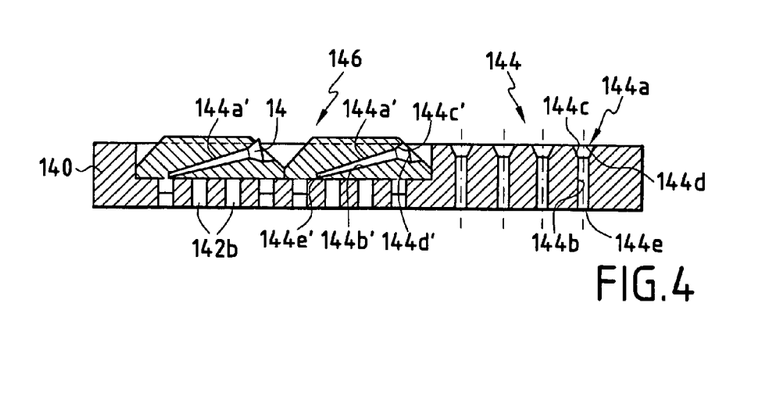
FIG. 4 is a section view on IV-IV of FIG. 2.

In particular, as can be seen in FIGS. 3 and 4, each cell 144a is formed by a cylindrical portion 144b of circular section and, in the vicinity of the opening of the cell 144a, by a frustoconically-shaped portion 144c, its conical shape flaring from said cylindrical portion 144b towards the opening 144d of the cell 144a.

The cells 144a shown in FIG. 1 extend along a vertical axis perpendicular to the support face 142a.

This also applies to cells 144a shown in FIGS. 2 to 4 that are situated in the second zone 144 defined in the bottom right corner of the storage space 130 as shown in FIG. 2.

Cells of this shape cannot be used when the screws are of a length that is greater than the thickness of the insert 140.

For such screws, a third zone 146 of the insert 140 is used, as can be seen in FIGS. 2 and 4. In this case, the cells 144a' extend in a longitudinal direction from an opening 144d' going down to the bottom 144e', with this longitudinal direction sloping relative to a plane parallel to the bottom wall 112 or to the support surface 142a.

In this way, the distance between the bottom 144e' and the opening 144d' of the sloping cell 144a' forms a hollow recess of length that is greater than the height of the insert 140 and the height of the side wall 114 of the bottom portion 112.

It should be observed that instead of having a cylindrical portion 144b of circular section, this portion may also be frustoconical in shape, tapering towards the bottom 144e: this is shown in FIGS. 2 and 4 for the sloping cells 144a'. Under such circumstances, the portion 144b' that is to receive the shank of the screw 14 flares much less than does the frustoconical portion 144c' that is to receive the head of the screw.

In the embodiment shown in FIG. 1, the housing means for storing the osteosynthesis kit 10 are constituted by the insert 140 which is made as a single piece presenting both the first zone 142 and the second zone 144.

Nevertheless, the storage space 130 could contain a plurality of inserts forming said housing means, and in particular at least a first insert fitted with the cavity 142 forming the first zone, and at least one second insert fitted with said cell 144a or a plurality of cells 144a in order to form the second zone 144.

For the embodiment shown in FIGS. 2 to 4, in addition to a first insert forming the first zone 142 and a second insert forming the second zone 144, the housing means further comprise a third insert 146 forming the above-mentioned third zone and defining at least one cell 144a' designed to receive an osteosynthesis screw of length that is greater than the cells 144a of the second insert 144 (second zone).

It should be understood that such a third insert 146 can either be formed integrally with the insert 140, or else it can be formed as one or more separate parts.

In a variant embodiment that is not shown, the cells 144a' of the third zone 146 of the insert 140 that are to receive long screws can also be constituted by a housing formed by a hollow surface provided with two flats that slope relative to each other and relative to the face of the support 142a, the shank and the head of an osteosynthesis screw coming to bear respectively against one or the other of the two sloping flats.

It will thus be understood that without modifying the bottom portion 110, it is possible to house one or more inserts specifically for housing one or more osteosynthesis plates and one or more osteosynthesis screws, which plates and screws may optionally be different or mutually identical.

Provision is also made for a heat-sealable film 150 to cover the free edge of the side wall 114 of the bottom portion 110 so as to enclose the storage space 130.

The presence of this film makes it possible to guarantee that the storage space 130 and the elements it contains remains sterile, while also making it possible to guarantee, by visual inspection, that this storage space 130 has not been opened previously.

The lid portion 120 (shown in FIG. 1) is constituted mainly by a wall for covering the opening of the storage space 130.

In order to be able to see inside the storage box 100, provision is made for the lid portion 120 to be transparent, at least in part, and preferably over its entire surface facing the opening of the bottom portion 110, i.e. facing the entire storage space 130.

Provision is advantageously also made for the lid portion 120 to be provided with a magnifying glass 122 integrated in its wall.

This magnifying glass 122 serves, before the box 100 is opened, to show in enlarged manner the zone of the storage space 130 that is situated in register with the magnifying glass 122.

In original manner, it is also possible to use the magnifying glass 122 to enlarge an image or a mention carried by a disk placed on the inside face of the lid portion 120 in register with the magnifying glass 122 (configuration not shown).

The lid portion 120 is mounted to move relative to the bottom portion 110 by a hinge 160 which is shown as forming a pivot.

Naturally other types of functional elements suitable for allowing the lid portion 120 to move relative to the bottom portion 110 could be used in the same manner as the hinge 160: for example, it is possible to use a slideway, so that the lid portion is made slidable relative to the bottom portion, or else a pivot having an axis that is not parallel to the longitudinal edge of the rectangle constituting the general shape of the lid portion 120 and the bottom portion 110, i.e. a pivot presenting an axis perpendicular to the support face 142a or to the bottom wall 112.

In order to keep the packaging and presentation box 100 of the present invention in the closed position (not shown), provision is also made for the bottom portion 110 and the lid portion 120 to present closure means 170.

Figure 6:
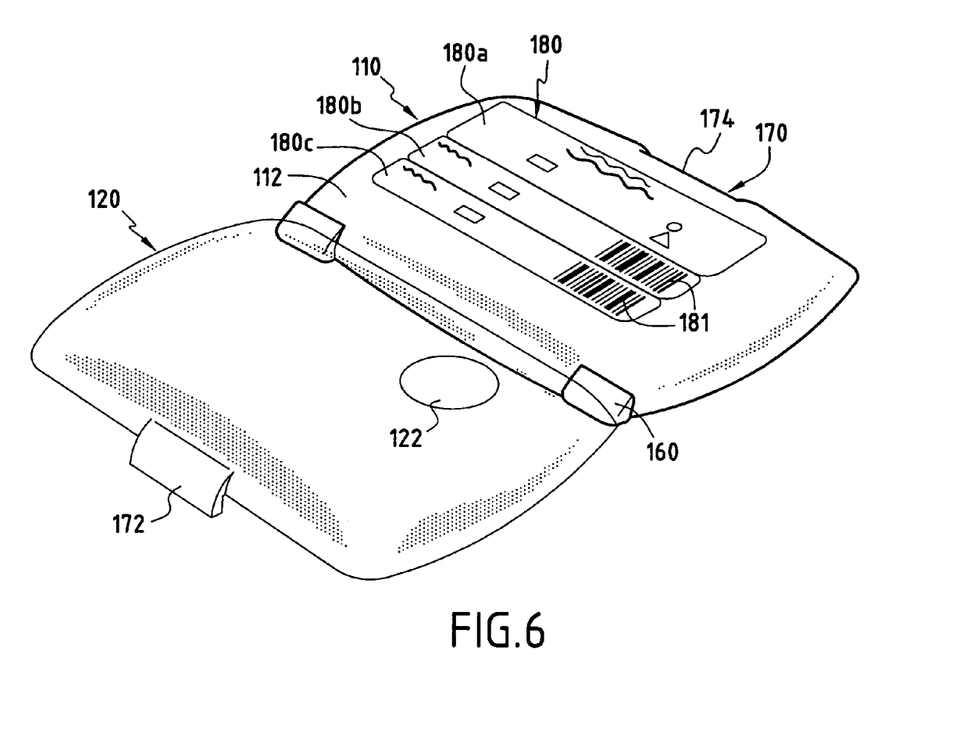
FIG. 6 is a perspective view of the FIG. 1 box seen from behind while in its open position.

In the embodiment shown, these closure means 170 are constituted by a system that clips by means of complementary shapes (see FIGS. 1 and 6). More precisely, the closure means comprise a tongue 172 placed along the edge of the lid portion 120 that is remote from the hinge 160, said tongue 172 being suitable for co-operating by means of its complementary shape with a notch 174 placed in the edge of the side wall 114 of the bottom portion 110, said edge facing away from the bottom wall 112 and the hinge 160.

In another aspect of the present invention, and as can be seen in FIG. 6, the face of the bottom wall 112 that faces away from said storage space 130 is provided with a label 180.

This label 180 forms an identification medium carrying information relating to said osteosynthesis kit 10, in particular in the form of a bar code.

More precisely, the label 180 is made up of three portions 180a, 180b, and 180c, each of which carries the reference of the company that prepared and sterilized the osteosynthesis kit 10 located inside the box 100.

Each of these portions 180a, 180b, and 180c carries a series of information items including the serial number of the box 100, the batch number, and the references of each of the elements (plates 12 and screws 14) making up the osteosynthesis kit 10, and information relating to the positions of each of the elements in the osteosynthesis kit amongst the various housings (cavity 142 and cells 144a, 144a').

Thus, after some of the elements making up the osteosynthesis kit 10 that is housed inside the box 100 have been used, it is possible to know which elements are missing in order to refill the box 100.

In addition, since the portions 180a, 180b, and 180c of the label 180 carries the same information, the portion 180a can be stored for archive purposes, while the portion 180b can be stuck on the patient's dossier, and the portion 180c can be used in the report on the operation.

Figure 7:
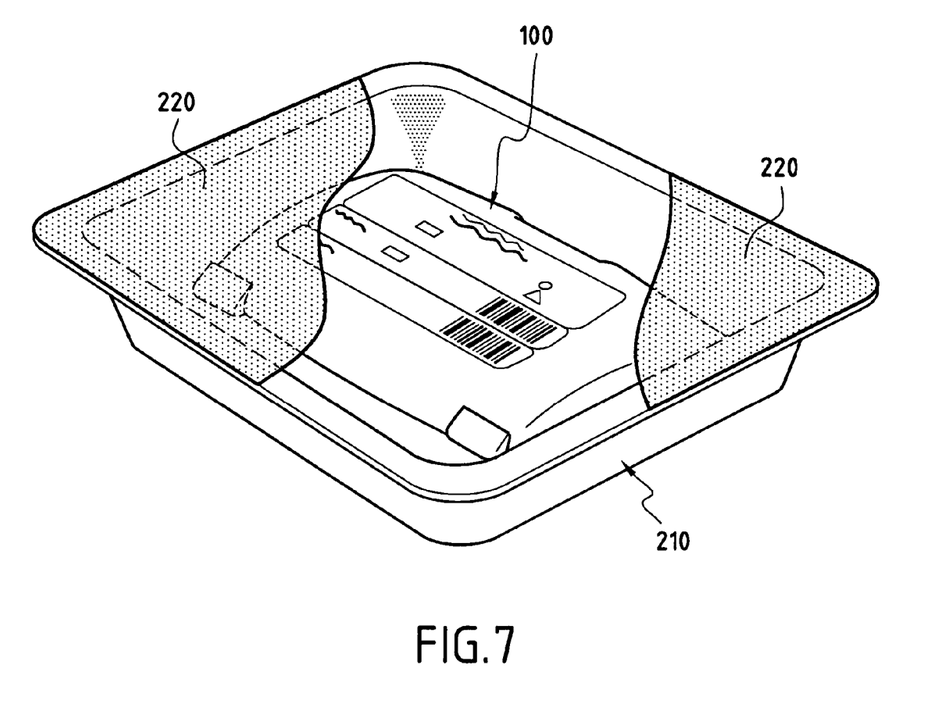
FIG. 7 is a perspective view from one of the corners and from above of a tray containing a box of the invention in order to form a protective unit.

In order to protect the packaging and display box 100 while it is being transported and before the osteosynthesis kit 10 it contains is used, the present invention also relates to a protective unit 200 which comprises not only the packaging box 100 as described above, but also:

- a tray 210 (see FIG. 7) preferably made of a transparent or translucent plastics material, said tray 210 defining a housing suitable for receiving the box 100, as can be seen in FIG. 7. This tray 210 is generally rectangular in shape and likewise comprises a bottom wall and a continuous side wall, and which projects upwards from the edges of the bottom wall and a heat-sealable film 210 serves to close the space defined by the tray 210 in sealed manner. The packaging box 100 is preferably placed in the space defined by the tray 210, with the label 180 facing towards the heat-sealable film 220 so that the label 180 remains visible through the heat-sealable film; and
- a protective and packaging case 230 (see FIG. 8) likewise made of preferably transparent or translucent plastics material, the case 230 likewise comprising a bottom portion and a lid portion that are movable relative to each other between an open position and a closed position, an external label 240 that is preferably situated on the side wall of the case 230 serving to form means enabling the type of osteosynthesis kit 10 contained in the packaging box 100 housed in the tray 210 to be identified visually when the tray is in place in the bottom portion of the case 230. For this purpose, a color code carried by the external label 240 may serve to designate a particular type of osteosynthesis kit 10.

In order to facilitate distribution of protective units 200 each comprising a respective packaging and display box 100, the present invention also provides for using a chest 300 (see FIG. 9) having a plurality of compartments 310a for receiving protective units 200 and a compartment 310b suitable for receiving, for example, surgical instruments for use during surgery involving the osteosynthesis kit 10 contained in the box 100 of one of the protective units 200.

Figure 8:
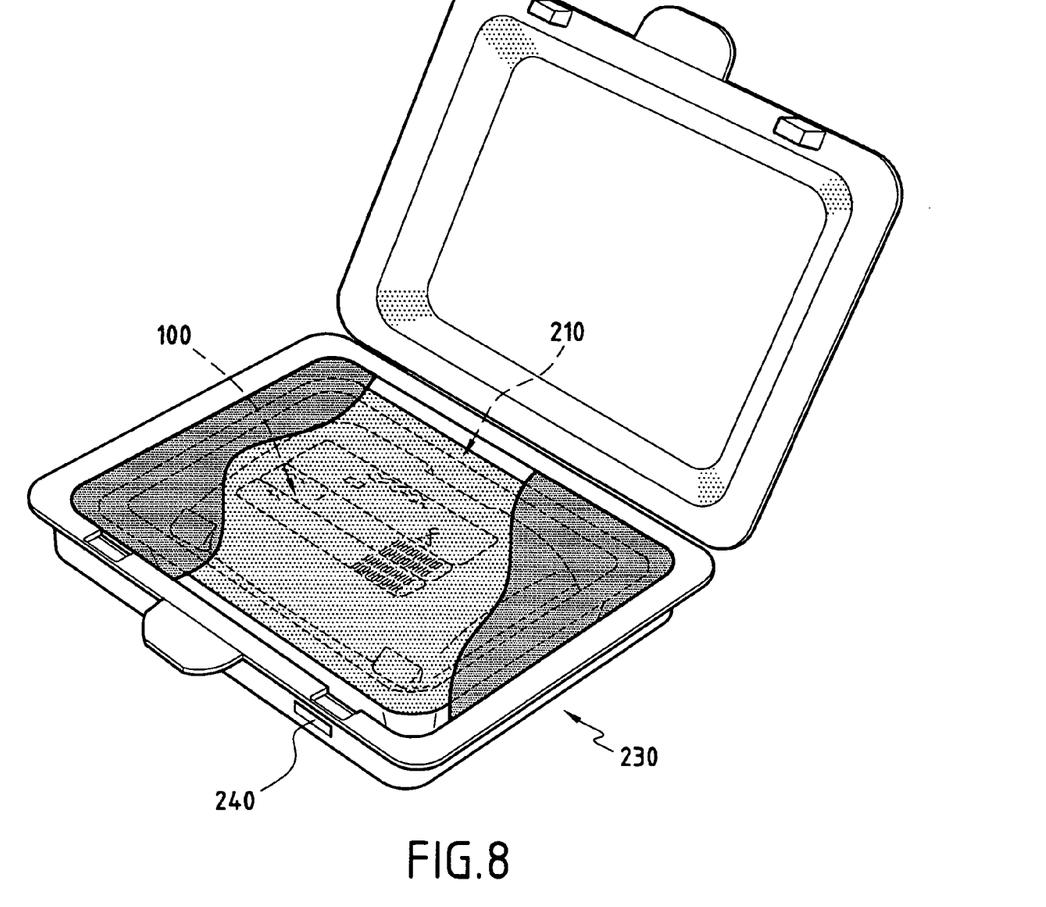
FIG. 8 is a perspective view from one of its corners and from above of a protective case containing the FIG. 7 tray, the case being shown in its open position, and forming a protective unit.

Thus, by means of the label 240 situated on each of the protective and packaging cases 230 forming the outer envelope of the protective units 200, it is possible quickly and simply to determine the particular type of osteosynthesis kit 10 that is contained in each protective unit 200 in order to select from the chest 300 the case containing the packaging and display box 100 containing the looked-for osteosynthesis kit.

Figure 9:
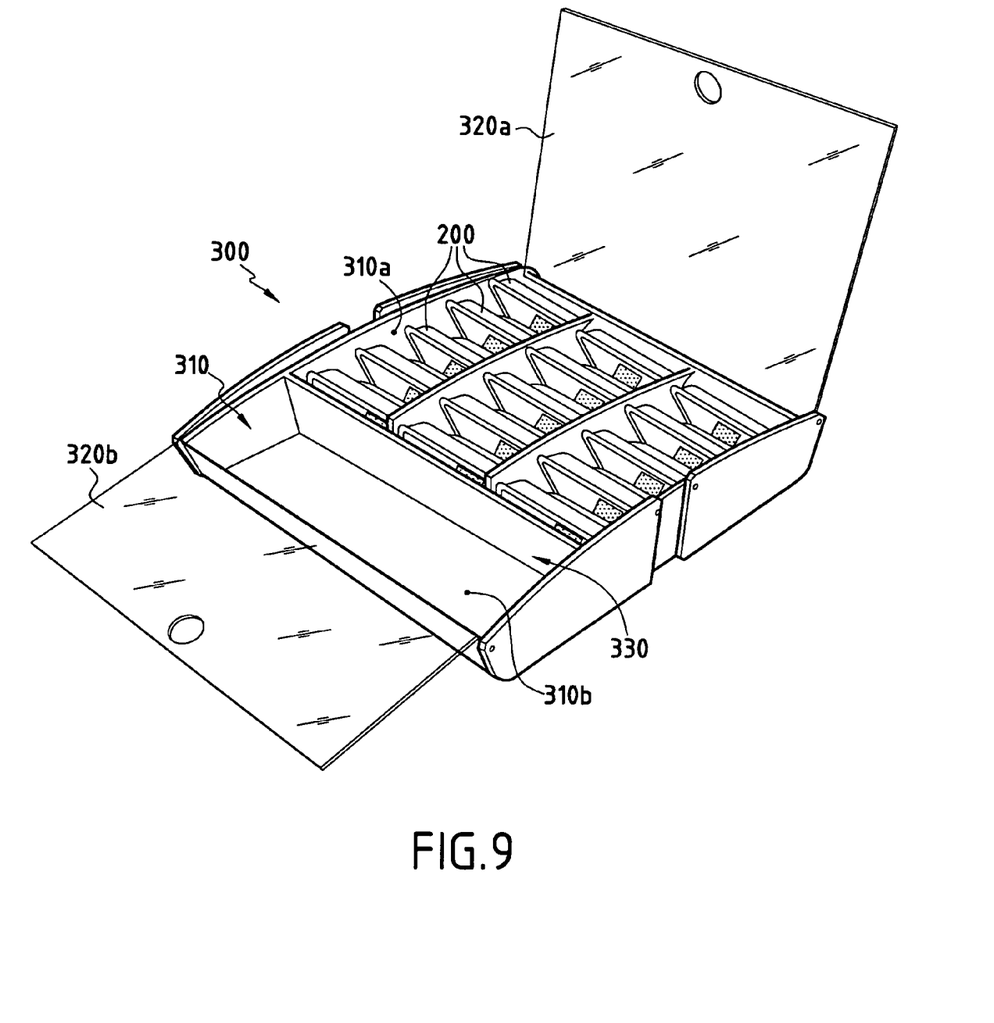
FIG. 9 is a perspective view from one of its corners and from above of an open display chest in which protective units as shown in FIG. 8 are stored.

In FIG. 9, the chest 300 also presents two lid portions 320a and 320b both of which are mounted to pivot relative to the free edge of the side wall of the bottom portion 310 so as to close in reversible manner the space 330 defined by the bottom portion 310.

It should be observed that the elements forming the osteosynthesis kit shown in the above-described embodiment should not be restricted to equipment for performing osteotomy, in particular of the lower jaw, but that it is appropriate to consider also using elements suitable for other kinds of maxillo-facial surgery, or more generally other kinds of osteosynthesis surgery.

Thus, in general manner, the osteosynthesis kit may comprise one or more plates and/or one or more screws and/or one or more pins and/or one or more metal wires, . . . .

The invention claimed is:

1. A packaging and display box for an osteosynthesis kit, said osteosynthesis kit comprising at least one plate and at least one osteosynthesis screw, wherein the box comprises a bottom portion and at least one lid portion, said bottom portion comprising a bottom wall and a side wall upwardly extending from the bottom wall around its entire periphery, thereby defining a storage space, functional means making said lid portion movable relative to said bottom portion between an open position and a closed position, wherein said box includes reversible closure means placed on said bottom portion and on said lid portion and suitable for co-operating in said closed position, housing means for housing said osteosynthesis kit, said housing means being suitable for being held in said storage space and comprising at least one insert, said housing means being provided with at least one cavity for receiving at least one osteosynthesis plate and at least one cell for receiving at least one osteosynthesis screw; and wherein said box includes a heat-sealable film enclosing said storage space.

2. A box according to claim 1, wherein said cavity includes a support face for supporting said osteosynthesis plate, which face is provided with hollow zones.

3. A box according to claim 2, wherein said support face is also provided with projecting zones.

4. A box according to claim 3, wherein said support face for supporting said osteosynthesis plate is provided with ribs and with grooves.

5. A box according to claim 1, wherein said cavity includes a support face for supporting said osteosynthesis plate, which face is provided with retaining means for co-operating reversibly with said osteosynthesis plate.

6. A box according to claim 1, wherein said face of the bottom wall facing away from said storage space is provided with an identification medium carrying information relating to said osteosynthesis kit.

7. A box according to claim 1, wherein said housing means are formed by a one-piece insert.

8. A box according to claim 1, wherein said housing means comprise at least one first insert including said cavity, and at least one second insert including said cell.

9. A box according to claim 8, wherein said housing means further comprise a third insert defining at least one cell for receiving an osteosynthesis screw.

10. A box according to claim 1, wherein said cell is formed by a hollow recess of shape that is complementary to said screw so that the head of the screw is situated in the opening of said recess.

11. A box according to claim 10, wherein said hollow recess presents a longitudinal direction going from its opening to its bottom, said longitudinal direction being inclined relative to said bottom wall so that the distance between the bottom and the opening of said hollow recess is longer than the height of the side wall of said bottom portion.

12. A box according to claim 1, wherein said lid portion is at least partially transparent.

13. A box according to claim 12, wherein said lid portion is provided with a magnifying glass integrated in its wall.

14. A protective unit comprising a packaging and display box for an osteosynthesis kit, said osteosynthesis kit comprising at least one plate and at least one osteosynthesis screw, wherein the box includes a bottom portion and at least one lid portion, said bottom portion comprising a bottom wall and a side wall upwardly extending from the bottom wall around its entire periphery, thereby defining a storage space, functional means making said lid portion movable relative to said bottom portion between an open position and a closed position, wherein said box includes: reversible closure means placed on said bottom portion and on said lid portion and suitable for co-operating in said closed position; housing means for housing said osteosynthesis kit, said housing means being suitable for being held in said storage space and comprising at least one insert, said housing means being provided with at least one cavity for receiving at least one osteosynthesis plate and at least one cell for receiving at least one osteosynthesis screw; wherein said protective unit includes a tray defining housing suitable for receiving said packaging and display box and provided with a heat-sealable film closing said housing.

15. A protective unit according to claim 14, wherein it further comprises a protective and packaging case suitable for surrounding said tray.

16. A protective unit according to claim 15, wherein said protective and packaging tray carries means for visually identifying the type of osteosynthesis kit contained in said packaging and display box.

17. A protective unit according to claim 14, wherein said protective case comprises a bottom portion and a lid portion that are movable relative to each other between an open position and a closed position, and in that said protective case further comprises reversible closure means disposed on said bottom portion and on said lid portion and suitable for co-operating in said closed position.

18. A display chest for distributing osteosynthesis kits, the display chest comprising a bottom portion fitted with compartments, wherein at least one compartment includes a protective unit comprising a packaging and display box for an osteosynthesis kit, said osteosynthesis kit comprising at least one plate and at least one osteosynthesis screw, wherein the box includes a bottom portion and at least one lid portion, said bottom portion comprising a bottom wall and a side wall upwardly extending from the bottom wall around its entire periphery, thereby defining a storage space, functional means making said lid portion movable relative to said bottom portion between an open position and a closed position; reversible closure means placed on said bottom portion and on said lid portion and suitable for co-operating in said closed position; and housing means for housing said osteosynthesis kit, said housing means being suitable for being held in said storage space and comprising at least one insert, said housing means being provided with at least one cavity for receiving at least one osteosynthesis plate and at least one cell for receiving at least one osteosynthesis screw, said protective unit further comprising a tray defining housing suitable for receiving said packaging and display box and provided with a heat-sealable film closing said housing, wherein said display chest includes at least one lid portion movable relative to said bottom portion and designed to close in reversible manner at least part of the space defined by the bottom portion.

* * * * *